(12) United States Patent
Arai et al.

(10) Patent No.: US 11,045,664 B2
(45) Date of Patent: Jun. 29, 2021

(54) RESIN LAMINATE RIDGE FILTER FOR PARTICLE THERAPY SYSTEM AND MANUFACTURING METHOD THEREOF

(71) Applicant: HITACHI, LTD., Tokyo (JP)

(72) Inventors: Satoshi Arai, Tokyo (JP); Hiroaki Furuichi, Tokyo (JP); Jun-ichi Hirai, Tokyo (JP); Osamu Chiba, Tokyo (JP); Tomoki Murata, Tokyo (JP)

(73) Assignee: HITACHI, LTD., Tokyo (JP)

(*) Notice: Subject to any disclaimer, the term of this patent is extended or adjusted under 35 U.S.C. 154(b) by 103 days.

(21) Appl. No.: 16/462,956

(22) PCT Filed: Nov. 28, 2017

(86) PCT No.: PCT/JP2017/042524
§ 371 (c)(1),
(2) Date: May 22, 2019

(87) PCT Pub. No.: WO2018/101237
PCT Pub. Date: Jun. 7, 2018

(65) Prior Publication Data
US 2019/0282830 A1 Sep. 19, 2019

(30) Foreign Application Priority Data
Dec. 2, 2016 (JP) .............................. JP2016-235246

(51) Int. Cl.
*A61N 5/10* (2006.01)
*B29C 64/124* (2017.01)
(Continued)

(52) U.S. Cl.
CPC ............. *A61N 5/10* (2013.01); *A61N 5/1042* (2013.01); *B29C 64/118* (2017.08);
(Continued)

(58) Field of Classification Search
None
See application file for complete search history.

(56) References Cited

U.S. PATENT DOCUMENTS 7,560,715 B2 * 7/2009 Pedroni ................... A61N 5/10
250/398
9,899,112 B2 2/2018 Takayanagi et al.
(Continued)

FOREIGN PATENT DOCUMENTS

CN 105705319 A 6/2016
CN 107005596 A 9/2017
(Continued)

OTHER PUBLICATIONS

Chinese Office Action received in corresponding Chinese Application No. 201780072351.5 dated Jul. 27, 2020.

*Primary Examiner* — James Choi
(74) *Attorney, Agent, or Firm* — Mattingly & Malur, PC

(57) ABSTRACT

A ridge filter 100 provided in a particle therapy system includes a repeating structure body 101 having a plurality of extending parts 101c extending along the incident direction P of a proton beam 204, and a bottom plate 102 provided on the lower face 101b side opposite to the incident side of the proton beam 204 of the repeating structure body 101. In addition, the repeating structure body 101 and the bottom plate 102 are integrally formed by a molding method, and each of the repeating structure body 101 and the bottom plate 102 is formed of a laminate of resin.

9 Claims, 12 Drawing Sheets

(51) Int. Cl.
  *B29C 64/153*   (2017.01)
  *B29C 67/00*   (2017.01)
  *B29C 64/268*   (2017.01)
  *B29C 64/118*   (2017.01)
  *B33Y 10/00*   (2015.01)
  *B33Y 80/00*   (2015.01)

(52) U.S. Cl.
  CPC .......... *B29C 64/124* (2017.08); *B29C 64/153* (2017.08); *B29C 64/268* (2017.08); *B29C 67/00* (2013.01); *A61N 2005/1095* (2013.01); *B33Y 10/00* (2014.12); *B33Y 80/00* (2014.12)

(56) References Cited

U.S. PATENT DOCUMENTS

| | | |
|---|---|---|
| 2015/0006098 A1 | 1/2015 | Ju |
| 2017/0243665 A1 | 8/2017 | Takayanagi et al. |
| 2018/0068753 A1* | 3/2018 | Kamiguchi .......... A61N 5/1042 |

FOREIGN PATENT DOCUMENTS

| | | | |
|---|---|---|---|
| JP | 2015-116284 A | 6/2015 | |
| JP | 2017-148204 A | 8/2017 | |
| JP | 2017-192669 A | 10/2017 | |
| WO | 2012/089706 A1 | 7/2012 | |
| WO | WO-2012089706 A1 * | 7/2012 | ............... A61N 5/10 |

* cited by examiner

RESIN LAMINATE RIDGE FILTER FOR PARTICLE THERAPY SYSTEM AND MANUFACTURING METHOD THEREOF

TECHNICAL FIELD

The present invention relates to a ridge filter used in a particle therapy system and a manufacturing method thereof.

BACKGROUND ART

A particle therapy system is an apparatus that irradiates a charged particle beam (hereinafter, also simply referred to as a beam) accelerated by an accelerator such as a synchrotron to cancer cells, and the demand has been rapidly expanded in recent years. In proton beam therapy, a scanning irradiation method has been spread, and is a method in which a target is divided into minute regions (spots) and a beam is irradiated onto each minute region. In the scanning irradiation method, only a target volume is irradiated by a high dose by appropriately controlling an irradiation point and an irradiation amount, and the surrounding normal tissue can be irradiated by decreasing the dose. A proton beam emits the maximum energy at a certain depth. Thus, in order to precisely adjust in the traveling direction of the beam, the energy of the accelerator is changed, or range shifters for adjusting a range are combined and used in addition to a change in energy of the accelerator.

In addition, a beam cannot be uniformly irradiated onto a target having a width in the depth direction because the beam forms dose distribution referred to as Bragg curve in the depth direction and is peaked at a certain depth. Therefore, it is necessary to expand a region of uniform dose distribution in the depth direction. As a countermeasure, control of the depth direction using a ridge filter has been known.

Japanese Unexamined Patent Application Publication No. 2015-116284 (Patent Literature 1) discloses a structure and a manufacturing method of a ridge filter, and Patent Literature 1 describes a structure and a manufacturing method of a ridge filter in which the ridge filter is manufactured by combining pieces produced by machining because the shape of the ridge filter is complicated.

CITATION LIST

Patent Literature

[Patent Literature 1] Japanese Unexamined Patent Application Publication No. 2015-116284

SUMMARY OF INVENTION

Technical Problem

In the case of using the manufacturing method of the ridge filter described in Patent Literature 1, the pieces each of which is formed by machining are fitted into each other, and thus are likely to be misaligned when being fitted. Accordingly, the yield is disadvantageously deteriorated. In addition, there is a problem that variations in characteristics are likely to occur due to the misalignment.

An object of the present invention is to provide a technique that can enhance the yield while enhancing the accuracy of characteristics in a ridge filter by using a lamination molding method when manufacturing the ridge filter to realize a structure of the ridge filter suitable for lamination molding thereof.

The above-described objects and novel features of the present invention will become apparent from the description of the specification and the accompanying drawings.

Solution to Problem

The following is a summary of the representative outline of embodiments disclosed in the application.

A ridge filter according to an embodiment includes a first structure body that includes a plurality of extending parts extending along the incident direction of a proton beam used for a particle therapy system, and a second structure body that is provided on any one of a first face of the first structure body on the incident side of the proton beam and a second face opposite to the first face. In addition, the first structure body and the second structure body are integrally formed, and each is formed of a laminate.

Further, a manufacturing method of a ridge filter according to an embodiment includes a step (a) of discharging molten resin from a nozzle, and a step (b) of sequentially repeating scanning of the nozzle in the direction intersecting with the lamination direction of the resin to form a bottom part by lamination molding of the resin. In addition, the method includes a step (c) of forming a plurality of extending parts each of which is formed of a laminate and extends in the lamination direction of the resin on the bottom part in the direction intersecting with the lamination direction of the resin to mold a structure body including the plurality of extending parts.

Further, a manufacturing method of a ridge filter according to another embodiment includes a step (a) of laying a resin powder, and a step (b) of irradiating a laser onto the laid resin powder and sequentially repeating sintering or melting by the irradiation of the laser to form a bottom part by lamination molding of the resin. In addition, the method includes a step (c) of forming a plurality of extending parts each of which is formed of a laminate and extends in the lamination direction of the resin on the bottom part in the direction intersecting with the lamination direction of the resin to mold a structure body including the plurality of extending parts.

Advantageous Effects of Invention

The following is a summary of an effect obtained by the representative invention among those disclosed in the application.

It is possible to manufacture a ridge filter with high accuracy.

DESCRIPTION OF EMBODIMENTS

First Embodiment

Figure 1:
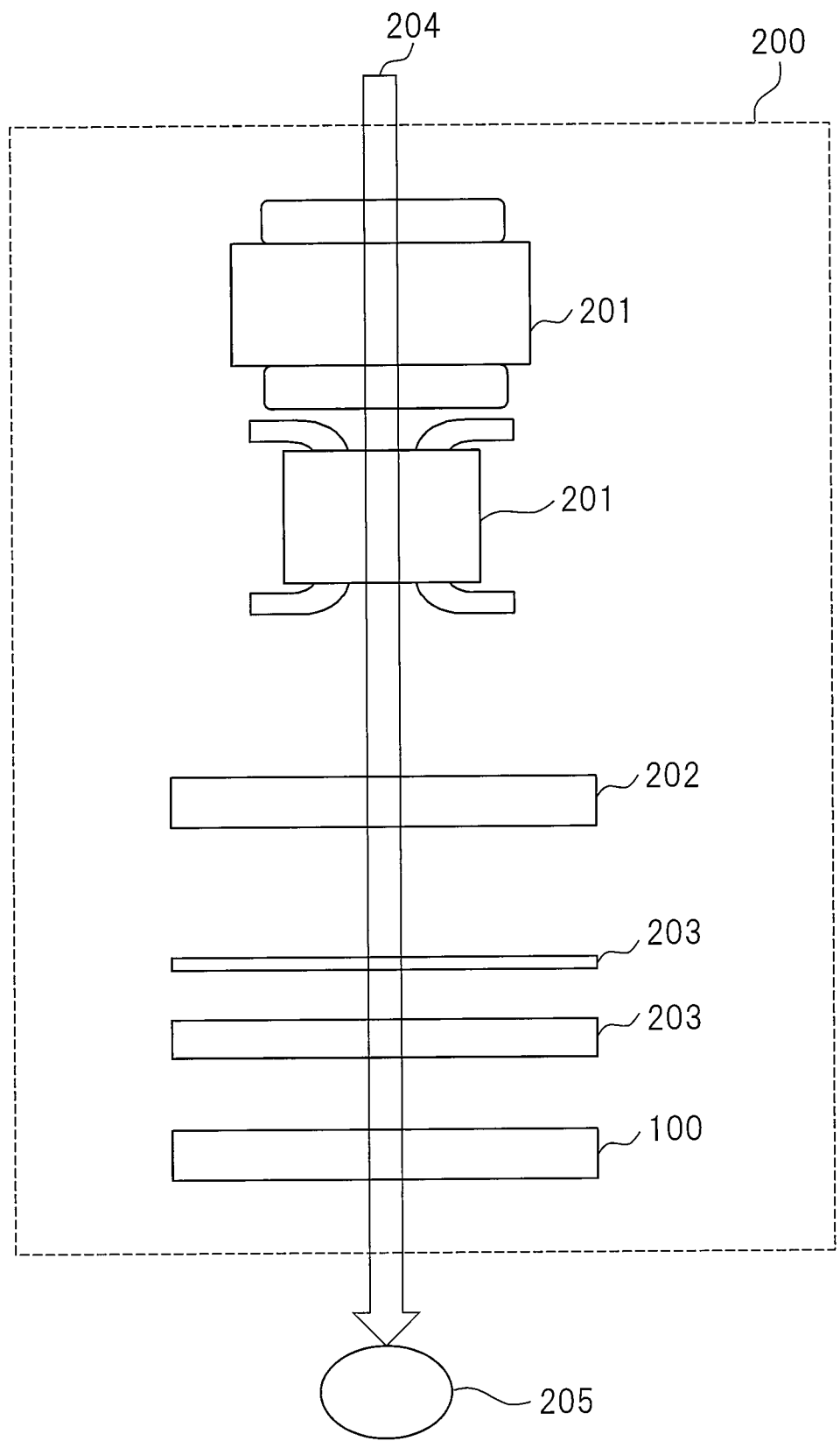
FIG. 1 is an outline view of a proton beam irradiation nozzle in which a ridge filter according to a first embodiment of the present invention is provided.

Hereinafter, a structure of a ridge filter and a manufacturing method of the ridge filter of a first embodiment will be described using the drawings. FIG. 1 is an outline view of a proton beam irradiation nozzle in which the ridge filter according to the first embodiment of the present invention is provided. It should be noted that FIG. 1 shows an irradiation nozzle 200 that is a main part of a particle therapy system to which the ridge filter of the first embodiment relates. The ridge filter is a filter member for a proton beam (beam) provided in the particle therapy system, and expands the width of the Bragg peak (the maximum part of an energy loss caused immediately before charged particles advancing in a substance stop) by overlapping beams having different arrival depths with each other.

A scanning magnet 201 that scans the advancing direction (depth direction) of a proton beam 204 that is a beam and the direction (horizontal direction) vertical to the beam is used for the irradiation nozzle 200. The beam (proton beam 204) scanned by the scanning magnet 201 is irradiated onto an irradiation target 205, namely, a target volume. A dose monitor 202 measures an irradiation amount of the charged particle beam irradiated onto each irradiation spot. A plurality of range shifters 203 is used while being combined with each other in many cases to adjust energy. The ridge filter 100 is arranged at a position closest to a patient in the irradiation nozzle 200. Resin is used for the range shifter 203 from the viewpoint of cost in many cases. However, for example, metal other than resin may be used as long as the material is resistant to the proton beam. On the other hand, the ridge filter 100 is desirably made of resin because the structure thereof is likely to be fine.

In the first embodiment, a lamination molding method is used as a manufacturing method of the ridge filter 100 shown in FIG. 4 to be described later. In the lamination molding method, molding time is extremely long, but an integrated structure can be produced (formed) and a shape that is difficult to be produced by machining can be produced. In addition, one of a molten deposition method in which actual thermoplastic resin can be used and a powder lamination method is desirably used as the lamination molding method.

The molten deposition method is a method in which molten thermoplastic resin is discharged from a nozzle to perform lamination molding. In general, amorphous resin is used, and ABS (acrylonitrile-butadiene-styrene copolymer), ASA (acrylonitrile-styrene-acrylic acid ester), PLA (polylactic acid), PC (polycarbonate), PPSF (polyphenyl sulfone), PEI (polyetherimide), alloy-based resin, and the like are used. In addition, in the case of the molten deposition method, a support (a part serving as a base when performing lamination molding, not shown in FIG. 1) is simultaneously used in molding. The support is used to suppress deformation during molding, and is removed after molding. As a method of removing the support, there is a method of mechanically removing the same, a method of dissolving the same in a liquid, or a method of removing the same using a blast or the like.

In addition, the powder lamination method is a method of performing lamination molding by repeating a process in which a resin powder is laid by a roller or a blade and a laser beam is irradiated onto the same, followed by melting and sintering. In the powder lamination method, amorphous resin is generally used from the viewpoint of accuracy and intensity, and PA12 (polyamide 12), PA11 (polyamide 11), PP (polypropylene), PE (polyethylene), POM (polyoxymethylene), PBT (polybutylene terephthalate), PA6 (polyamide 6), PA6-6 (polyamide 6-6), PPS, PEEK, and the like are used. However, an alloy or a blend with amorphous resin may be used as long as crystalline resin is a main material.

On the other hand, the ridge filter 100 of the first embodiment is preferably as small as possible in specific gravity in the viewpoint of minimizing the attenuation of the proton beam. Therefore, the specific gravity of the material required for the ridge filter 100 is less than 1.2, and is more preferably less than 1.1. Therefore, more preferable materials are ABS and ASA in the case of the molten deposition method, and are PA12, PA11, PP, and PE in the case of the powder lamination method. In both cases, inorganic materials may be slightly contained as long as the specific gravity is considered.

The ridge filter 100 of the first embodiment is characterized in that the ridge filter 100 is produced (formed) as an integrated structure by using the molten deposition method or the powder lamination method.

Figure 2:
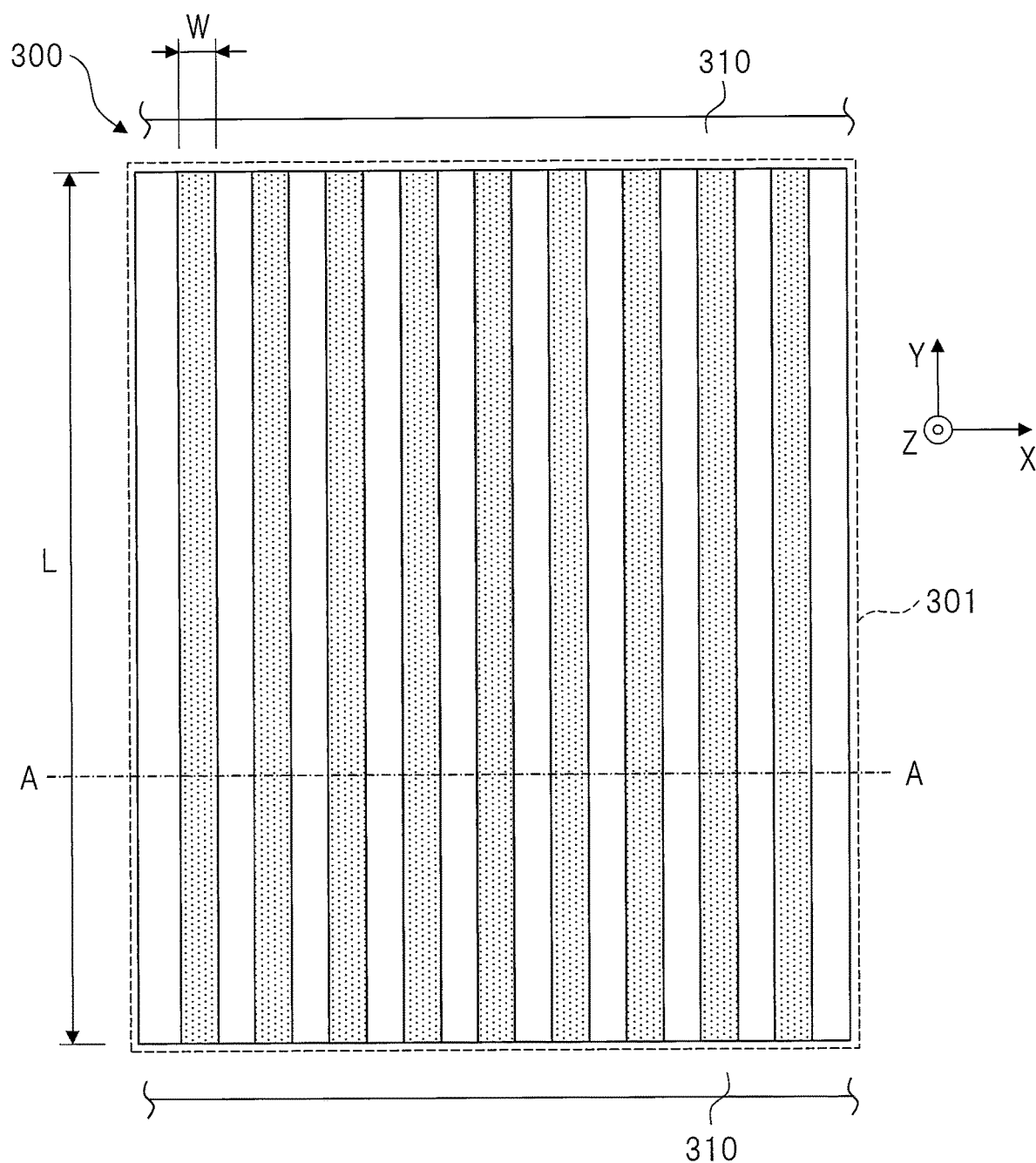
FIG. 2 is a plan view for showing a structure of a ridge filter of a comparative example.
Figure 3:
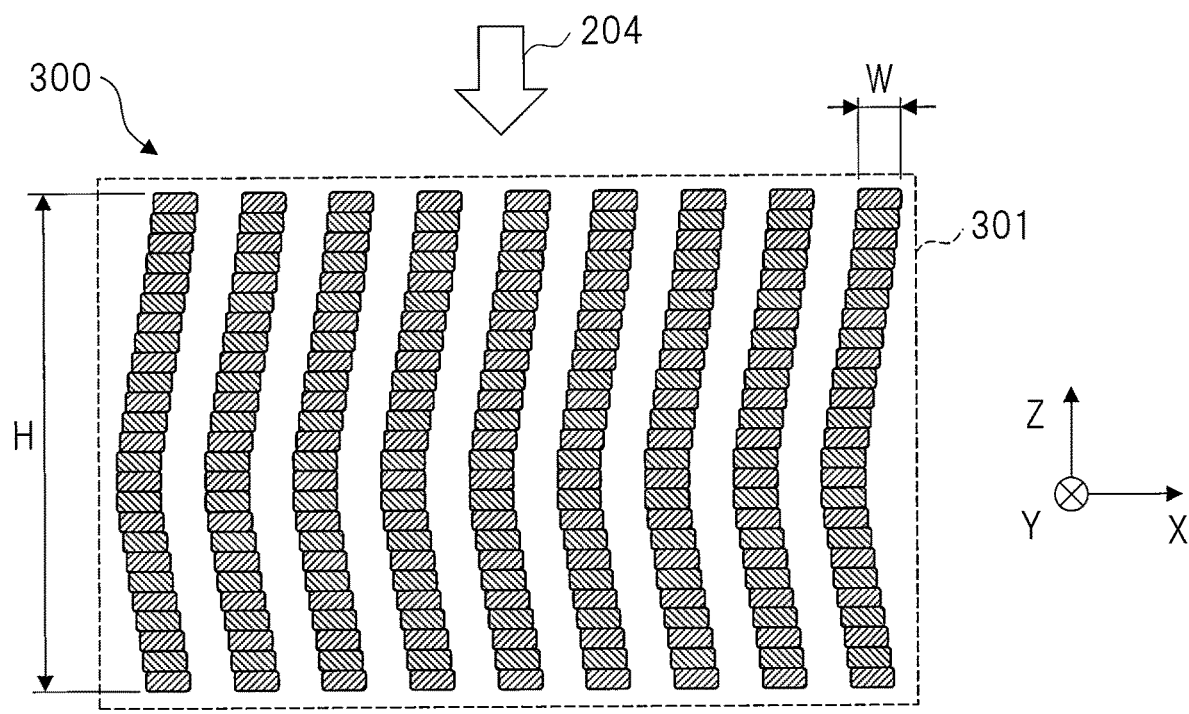
FIG. 3 is a cross-sectional view for showing a structure obtained by being cut along the line A-A of FIG. 2.

Here, FIG. 2 is a plan view for showing a structure of a ridge filter of a comparative example in which the inventors of the specification compared and examined, and FIG. 3 is a cross-sectional view for showing a structure obtained by being cut along the line A-A of FIG. 2. FIG. 2 and FIG. 3 show structure examples of a ridge filter 300 produced by the molten deposition method. In the case of the ridge filter 300 having the prototype structure, since the depth length L of a repeating structure body 301 was long and the width W of the ridge part was small, rigidity could not be held even if the ridge filter 300 could be normally formed using resin. In addition, the repeating structure body 301 between frames 310 of the ridge filter 300 provided to face each other was deflected when the ridge filter 300 was moved after installation, and thus the inventors found that desired characteristics could not be stably obtained. Further, a part of the repeating structure body 301 was deflected at a certain probability at the time of peeling the support, and the yield is disadvantageously deteriorated.

Accordingly, in the first embodiment, the high-accuracy ridge filter 100 can be formed by a structure and a manufacturing method of the ridge filter 100 to be shown below, and it is possible to provide the ridge filter 100 by which desired characteristics can be stably obtained.

Figure 4:
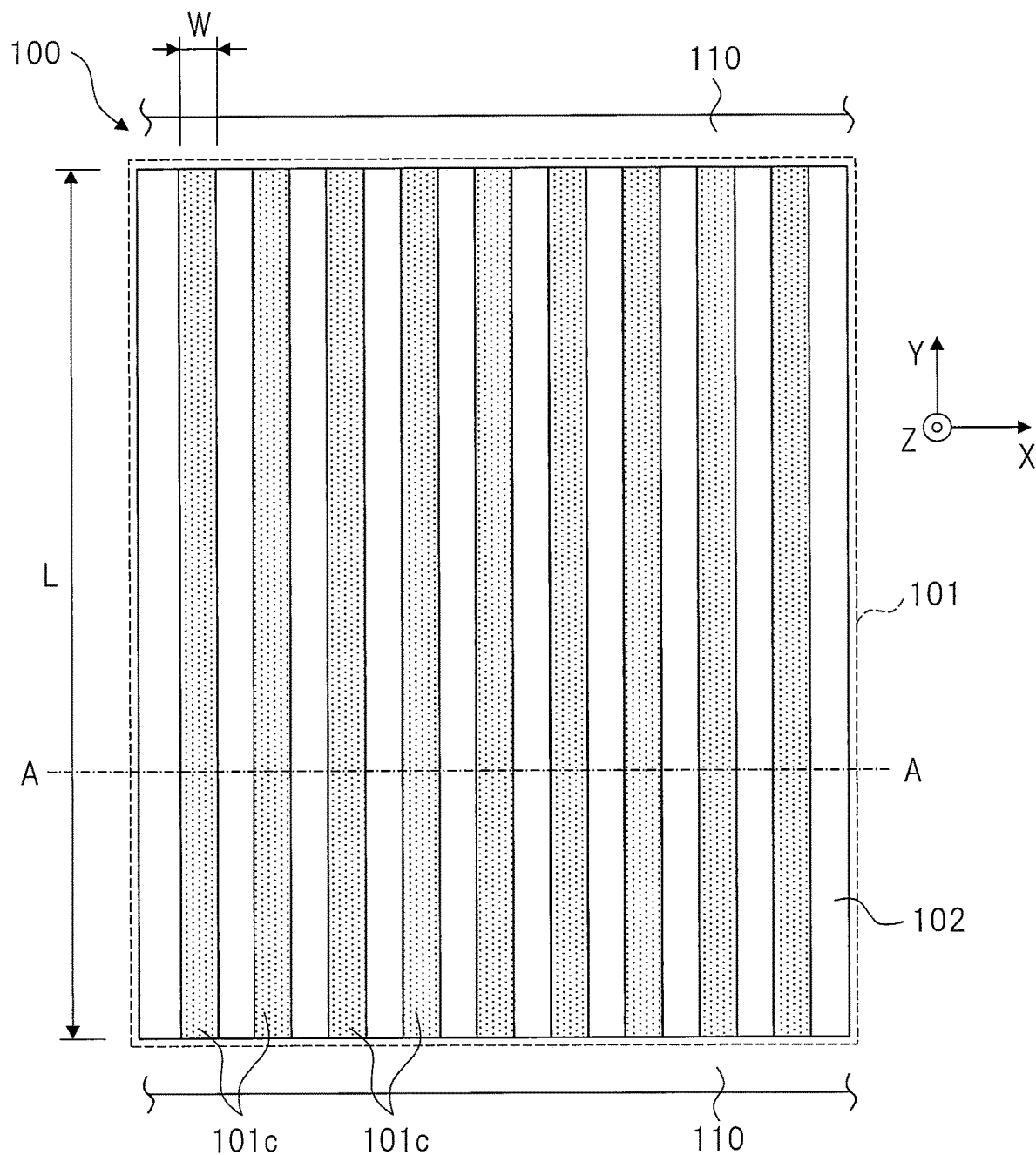
FIG. 4 is a plan view for showing an example of a structure of the ridge filter according to the first embodiment of the present invention.
Figure 5:
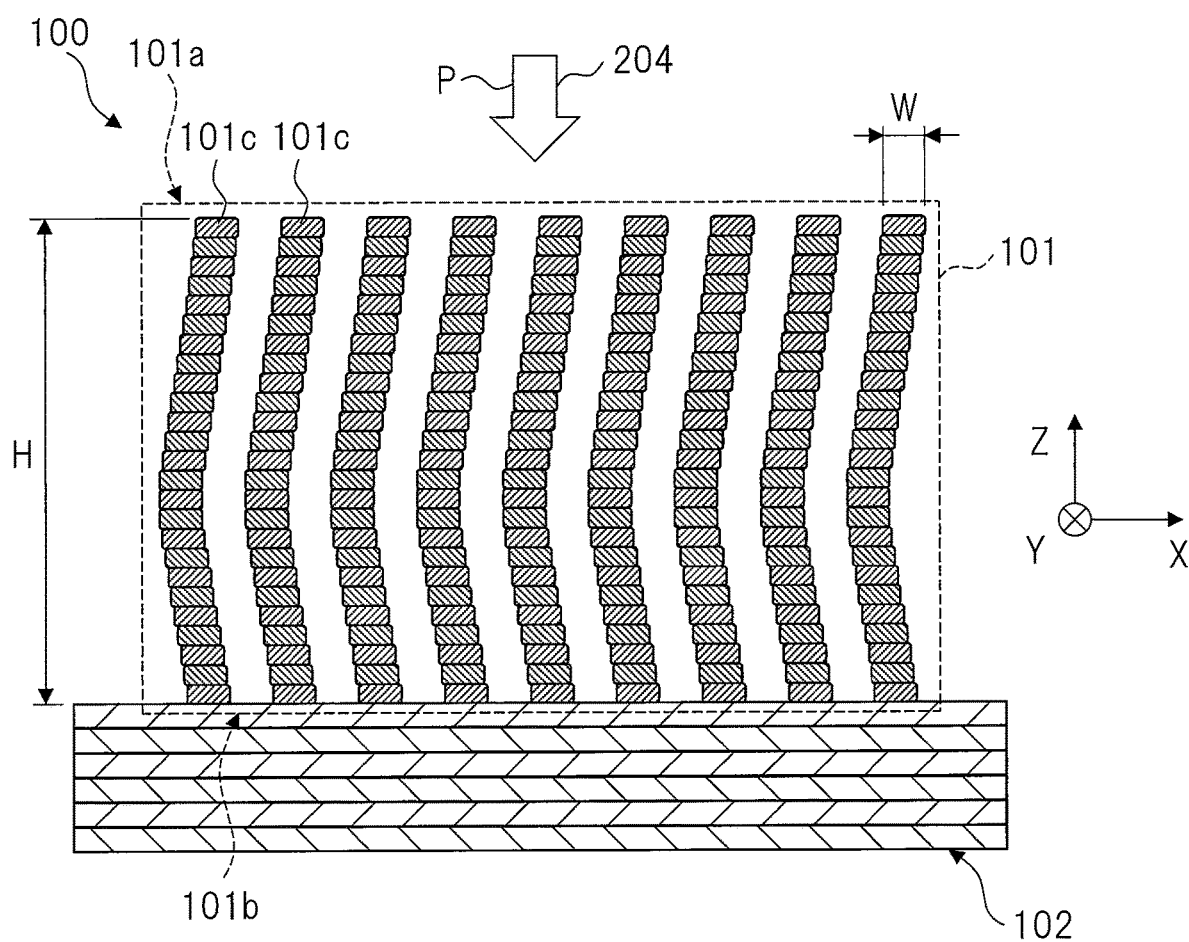
FIG. 5 is a cross-sectional view for showing a structure obtained by being cut along the line A-A of FIG. 4.

FIG. 4 is a plan view for showing an example of a structure of a ridge filter according to the first embodiment of the present invention, and FIG. 5 is a cross-sectional view for showing a structure obtained by being cut along the line A-A of FIG. 4. Namely, the ridge filter 100 shown in FIG. 4 is a structure example of the ridge filter 100 of the first embodiment to solve the above-described problems.

The ridge filter 100 shown in FIG. 4 and FIG. 5 has a repeating structure body (first structure body) 101 including a plurality of extending parts (ridge parts) 101c extending along an incident direction P of a proton beam 204 used for a particle therapy system. Further, the ridge filter 100 has a bottom plate (a bottom part or a second structure body) 102 provided on one of an upper face (first face) 101a of the repeating structure body 101 on the incident side of the proton beam 204 and a lower face (second face) 101b located at a position opposite to the upper face 101a. In the description of the first embodiment, the bottom plate 102 is provided on the lower face 101b.

In addition, the repeating structure body 101 and the bottom plate 102 are integrally formed, and each one is formed of a laminate.

Namely, the plurality of extending parts 101c each extending along the incident direction P of the proton beam 204 is provided, and at a bottom part of the repeating structure body 101 formed by a lamination molding method such as a molten deposition method or a powder lamination method, the bottom plate 102 is formed using the same material as the repeating structure body 101 by the lamination molding method same as the above, so that each of the repeating structure body 101 and the bottom plate 102 is formed of a laminate. Further, the repeating structure body 101 and the bottom plate 102 are integrally formed. In addition, a frame 110 is arranged around the repeating structure body 101.

As shown in FIG. 4, each of the plurality of extending parts 101c is formed in an elongated rectangular shape having a length L and a width W in planar view, and has a height H as shown in FIG. 5. In addition, the plurality of extending parts 101c is provided at predetermined pitches with respect to the X direction. Namely, the plurality of extending parts 101c is arranged at predetermined intervals with respect to the X direction.

According to the ridge filter 100 having the structure, the problem that the repeating structure body 101 is deflected at the time of peeling the support after molding can be suppressed, and the rigidity of the ridge filter 100 can be improved. Accordingly, the deflection does not occur at the time of moving the ridge filter 100, and desired characteristics of the ridge filter 100 can be stably obtained.

Namely, the ridge filter 100 can be manufactured with high accuracy. In addition, desired dose distribution can be stably obtained. Thus, the accuracy of the characteristics in the ridge filter 100 can be enhanced. Further, the cost of the ridge filter 100 can be reduced by forming the ridge filter 100 by the lamination molding method. In addition, the yield of the ridge filter 100 can be enhanced by forming the ridge filter 100 by the lamination molding method. Further, the shape of the ridge filter 100 can be secured by forming the ridge filter 100 by the lamination molding method. As a result, the shape of the ridge filter 100 can be inspected by the appearance.

It should be noted that the thickness of the bottom plate (the bottom part and the second structure body) 102 is desirably 0.1 mm or lager and 1.2 mm or smaller from the viewpoint of satisfying both of the attenuation of the proton beam 204 and the securement of the rigidity in the ridge filter 100 of the first embodiment. The bottom plate 102 can be manufactured as long as the thickness is 0.1 mm from the viewpoint of manufacturing.

Second Embodiment

Figure 6:
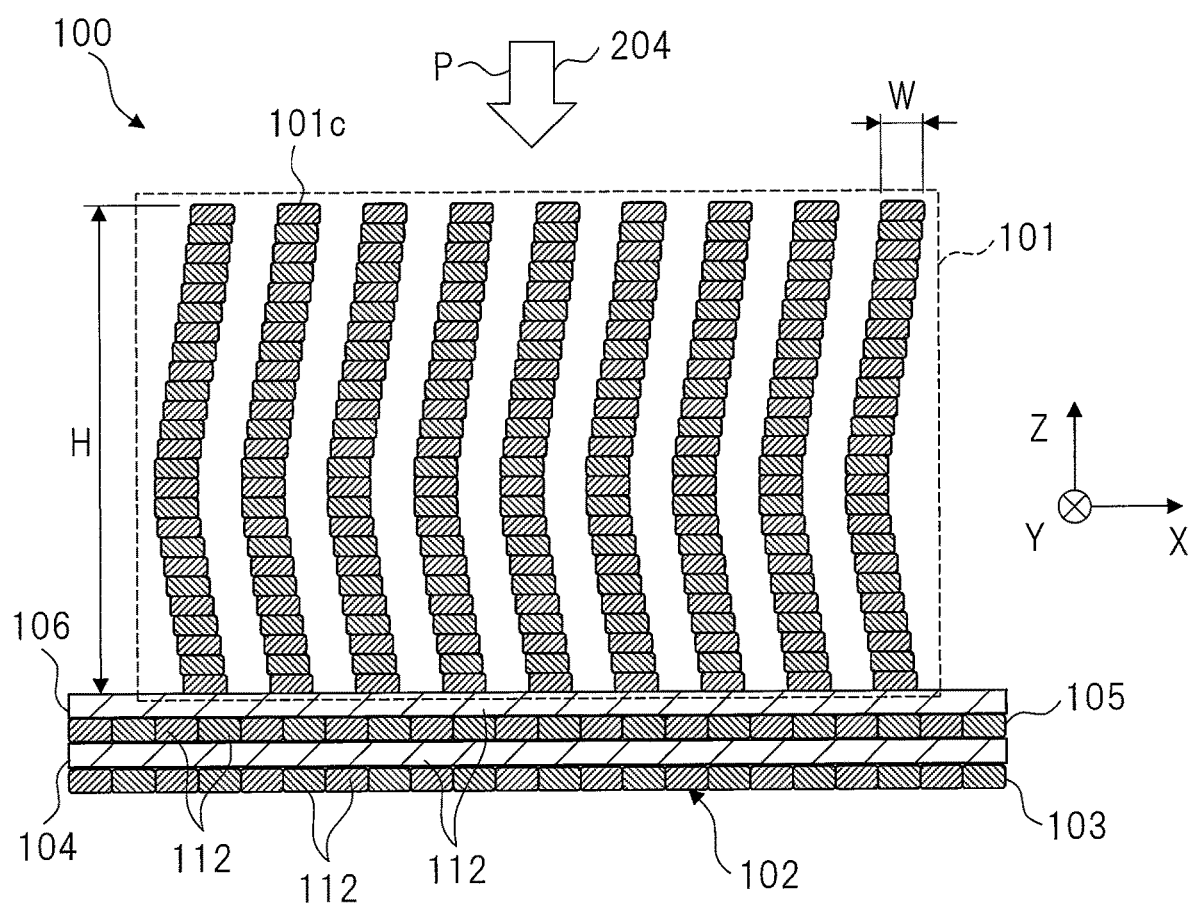
FIG. 6 is a cross-sectional view for showing an example of a structure of a ridge filter according to a second embodiment of the present invention.
Figure 7:
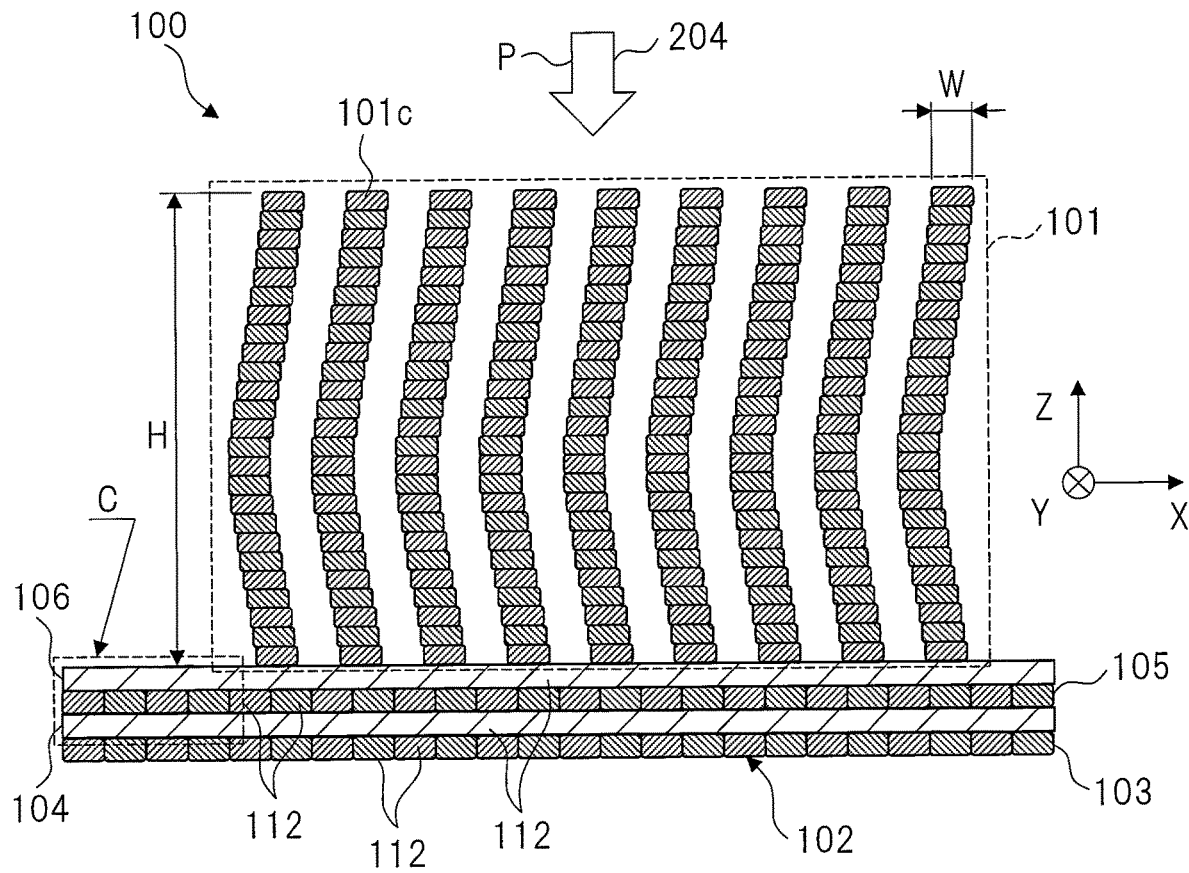
FIG. 7 is a cross-sectional view for showing a structure of a modified example of the ridge filter according to the second embodiment of the present invention.
Figure 8:
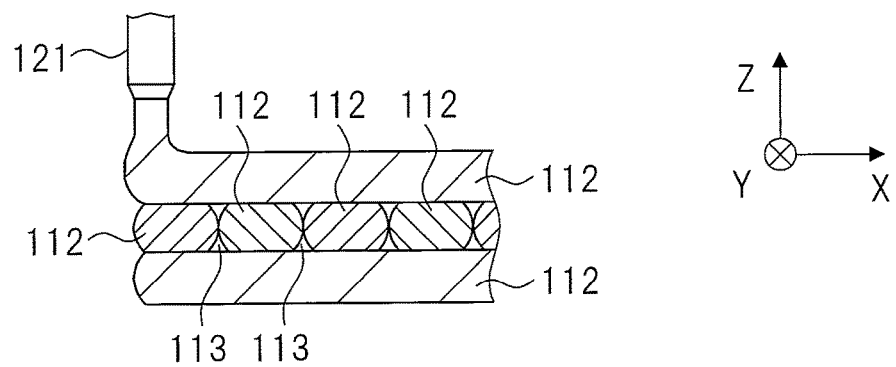
FIG. 8 is an enlarged part cross-sectional view shown by enlarging a molding method of a structure denoted by "C" of FIG. 7.

FIG. 6 is a cross-sectional view for showing an example of a structure of a ridge filter according to a second embodiment of the present invention, FIG. 7 is a cross-sectional view for showing a structure of a modified example of the ridge filter according to the second embodiment of the present invention, and FIG. 8 is an enlarged part cross-sectional view shown by enlarging a molding method of a structure denoted by "C" of FIG. 7.

In the case of the molten deposition method in the lamination molding method, voids (gaps) 113 are disadvantageously generated in resin in the direction vertical to the travelling direction of the resin discharged from a nozzle 121 shown in FIG. 8. Therefore, if the scan direction of the nozzle 121 is controlled only in one direction when forming a bottom plate 102 formed of a laminate of a resin 112, the voids 113 regularly remain at the same parts, and it is disadvantageous to obtain stable transmission characteristics of a proton beam 204 in some cases. Namely, if the voids 113 regularly exist, the fundamental structure becomes different. Accordingly, a ridge filter 100 of the second embodiment shown in FIG. 6 has a structure in the case of considering these problems, and is characterized in that as the scan directions of the nozzle 121, a first layer (lowermost layer) 103 of a bottom plate 102 is controlled in the Y direction, a second layer 104 is controlled in the X direction, a third layer 105 is controlled in the Y direction, a fourth layer 106 is controlled in the X direction, and these are sequentially repeated in the lamination direction (Z direction). Namely, the nozzle 121 is controlled to scan in the direction where the extending direction (the X direction or the Y direction) of the resin 112 alternately intersects with the lamination direction (Z direction) of the resin 112 as shown in FIG. 8. Accordingly, the extending direction of the resin 112 is formed so as to alternately intersect with the lamination direction of the resin 112. In other words, the resin 112 is molded so as to be in a mesh shape.

As described above, the regularity of the remaining voids of the bottom plate 102 can be reduced by controlling the scanning of the nozzle 121, and thus stable transmission characteristics of the proton beam 204 can be provided. In addition, the regular voids 113 generate the anisotropy of intensity, and thus the anisotropy can be reduced. In the case of the structure of the second embodiment, the number of laminated resins 112 is desirably an even number in the thickness of the bottom plate 102 from the viewpoint of the voids 113. The number of laminated resins 112 is desirably an even number because the X direction and the Y direction of the scanning of the nozzle can be regarded as a pair in the control of the nozzle 121.

As described above, the resin 112 is molded so as to be in a mesh shape by setting the number of laminated resins 112 to an even number. Accordingly, it is possible to prevent the voids 113 from being biased and closely arranged, and the intensity of the bottom plate 102 in the face direction can be uniformed.

It should be noted that in the viewpoint of setting the concrete thickness per layer of the resin 112 of the bottom plate 102, the thickness per layer is preferably set to be 0.1 mm to 0.3 mm in the case of the molten deposition method. In the case where the thickness is smaller than 0.1 mm, it is difficult to control. In the case where the thickness is larger than 0.3 mm, the intensity is likely to be decreased because the layer is too thick. However, if the thickness is set as described above, the ridge width cannot be formed by only one discharge from the nozzle 121 in some cases depending on a structure such as the fine width W of the extending part 101*c* of the repeating structure body 101 or an angle of a dogleg (bending) of the extending part 101*c*. In this case, it is preferable that the nozzle 121 is operated in one direction (Y+ direction of FIG. 4), the nozzle 121 is thereafter operated in the reverse direction (Y− direction of FIG. 4), and these are repeated. Further, the center positions of the resins 112 discharged from the nozzle 121 of FIG. 8 may be shifted from each other every other layer of the laminated layers as shown in FIG. 7 in order to reduce the regularity of the voids 113. Namely, the center of the resin 112 of the first layer 103 discharged from the nozzle 121 may be shifted from the center of the resin 112 of the third layer 105 discharged from the nozzle 121. In this case, the same applies to the resin 112 of the second layer 104 and the resin 112 of the fourth layer 106 although not shown in the drawing.

By shifting the centers of the resins 112 from each other every other layer as described above, the bias of the arrangement of the voids 113 can be reduced, and the intensity can be uniformed by reducing the bias of the intensity in the face direction of the bottom plate 102.

Third Embodiment

Figure 9:
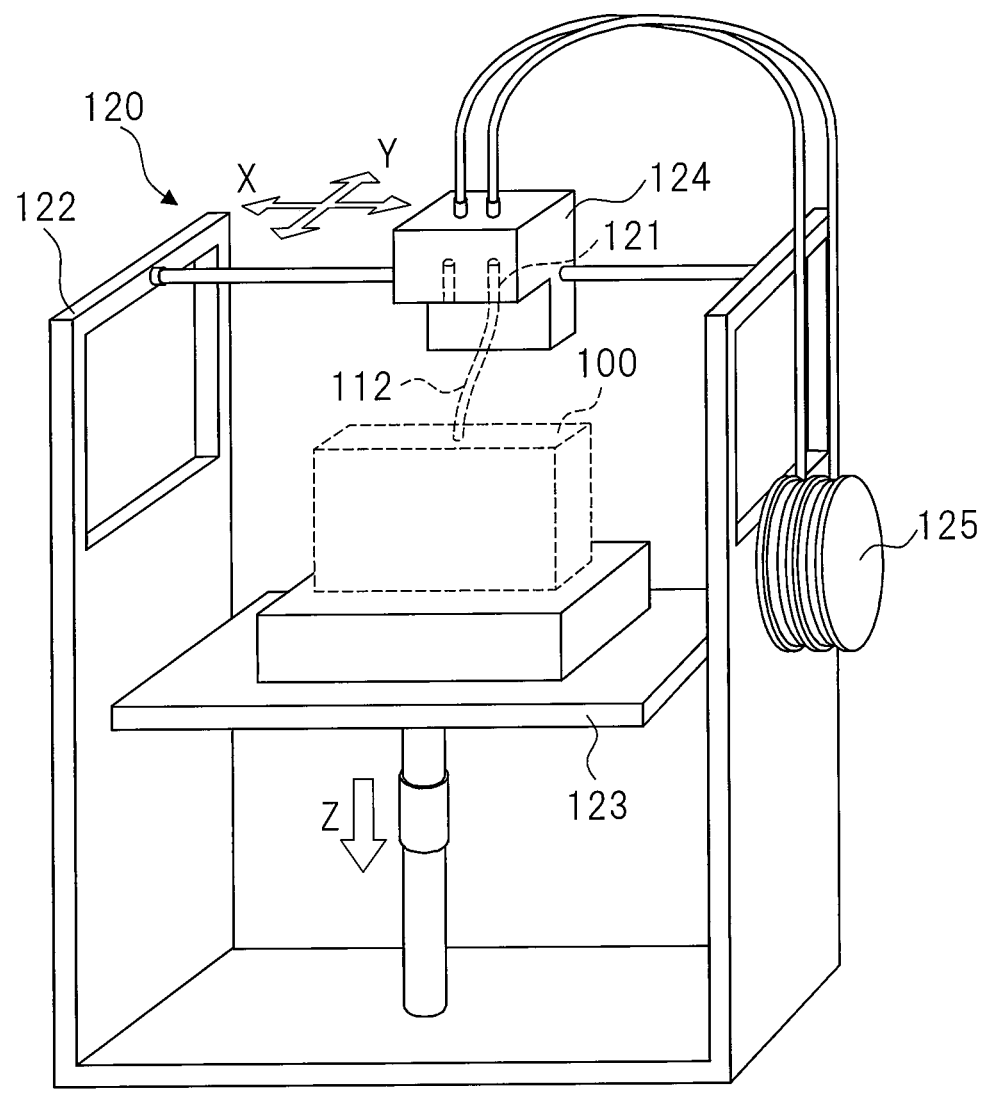
FIG. 9 is a perspective view for showing a lamination molding apparatus used in a molten deposition method according to a third embodiment of the present invention.
Figure 10:
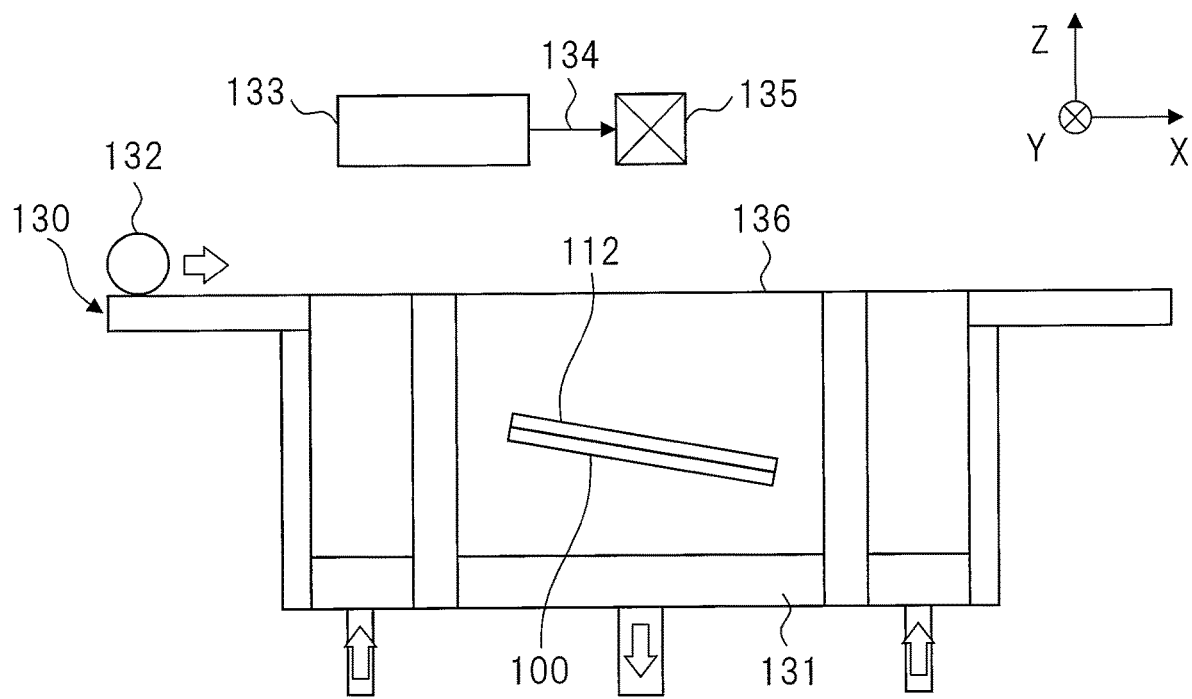
FIG. 10 is a schematic view for showing a lamination molding apparatus used in a powder lamination method according to the third embodiment of the present invention.

FIG. 9 is a perspective view for showing a lamination molding apparatus used in a molten deposition method according to a third embodiment of the present invention, and FIG. 10 is a schematic view for showing a lamination molding apparatus used in a powder lamination method according to the third embodiment of the present invention.

A molding method by the molten deposition method will be described using FIG. 9.

First, in a lamination molding apparatus 120 used in the molten deposition method, a resin 112 wound around a spool 125 of the lamination molding apparatus 120 is discharged in a molten state from a nozzle 121 of a head 124 installed on a molding table 123 in a chamber 122 of the lamination molding apparatus 120. In addition, the bottom plate 102 shown in FIG. 5 is formed by the lamination molding of the resin 112 by sequentially repeating the scanning of the nozzle 121 in the direction (the X direction or the Y direction) intersecting with the lamination direction (Z direction) of the resin 112. At this time, the bottom plate 102 is molded by the lamination molding of the resin 112 while changing the scan direction of the nozzle 121 so as to alternately intersect with each other for each layer.

Next, a repeating structure body 101 including a plurality of extending parts 101*c* is molded by forming the plurality of extending parts 101*c* each of which is formed of a laminate and extends in the lamination direction of the resin 112 on the bottom plate 102 shown in FIG. 5 in the direction intersecting with the lamination direction of the resin 112. Accordingly, a ridge filter 100 which is formed of a laminate of the resin 112 and in which the bottom plate 102 and the repeating structure body 101 are integrally formed is formed.

In addition, the bottom plate 102 is desirably molded by laminating the layers of the resin 112 the even number of times as described in the second embodiment. Accordingly, it is possible to prevent the voids 113 shown in FIG. 8 from being biased and closely arranged.

It should be noted that in the case where the size of the ridge filter 100 is increased, the resin 112 is warped after molding in some cases when a support (a part serving as a base when performing lamination molding) is removed. When the resin 112 is warped, ununiformity of transmission of a proton beam 204 is disadvantageously increased. In such a case, it is preferable that the ridge filter 100 after molding is entirely pressurized to be corrected flat by reducing the density of the bottom plate 102 as compared to that of the repeating structure body 101. Namely, the void fraction of the bottom plate 102 is made larger than that of the repeating structure body 101, and the rigidity of the bottom plate 102 is made smaller than that of the repeating structure body 101. Thereby, flattening of the bottom plate 102 can be easily corrected. In other words, since the bottom plate 102 and the repeating structure body 101 are formed of the resins 112 and the voids 113 as shown in FIG. 8, the ratio of the resin 112 in the bottom plate 102 is made smaller than that in the repeating structure body 101.

In addition, in this case, the elastic modulus of the bottom plate 102 becomes smaller than that of the repeating structure body 101. At the time of pressurizing, a flat plate may be crept (plastically deformed) by being pressurized for a long time. Alternatively, a load may be applied while heating after considering the temperature at which flexure occurs due to the load. In this case, it is desirable that the structure of the second embodiment is simultaneously used. In addition, the molten deposition method is disadvantageous in productivity due to a long modeling time. In such a case, the productivity can be improved by increasing the amount of resin discharged from the nozzle 121 only for the bottom plate 102 or increasing the size of the nozzle.

In the above-described first to third embodiments, a structure and a manufacturing method of the ridge filter 100 manufactured by the molten deposition method have been described. Next, a molding method by a laser lamination molding method will be described using FIG. 10.

First, in a lamination molding apparatus 130 used in the laser lamination molding method, a resin powder 136 is laid on a molding table 131 by a roller 132. Next, a laser 134 is irradiated onto the laid resin powder 136 from a laser light source 133. At this time, the laser 134 is irradiated onto the resin powder 136 by changing the angle of the laser 134 by a mirror 135. Then, the bottom plate 102 shown in FIG. 5 is formed by the lamination molding of the resin 112 by sequentially repeating sintering or melting with irradiation of the laser 134.

Next, the repeating structure body 101 including the plurality of extending parts 101*c* is molded by forming the plurality of extending parts 101*c* each of which is formed of a laminate and extends in the lamination direction of the resin 112 on the bottom plate 102 in the direction (the X direction or the Y direction) intersecting with the lamination direction (Z direction) of the resin 112. Accordingly, the ridge filter 100 which is formed of a laminate of the resin 112 and in which the bottom plate 102 and the repeating structure body 101 are integrally formed is formed.

In addition, the energy density of the laser 134 irradiated when molding the bottom plate 102 is made smaller than that of the laser 134 irradiated when molding the repeating structure body 101 to perform the lamination molding.

In other words, the void fraction of the bottom plate 102 is made larger than that of the repeating structure body 101, and the rigidity of the bottom plate 102 is made smaller than that of the repeating structure body 101. Thereby, flattening of the bottom plate 102 can be easily corrected. In other words, since the bottom plate 102 and the repeating structure body 101 are formed of the resins 112 and the voids 113 as shown in FIG. 8, the ratio of the resin 112 in the bottom plate 102 is made smaller than that in the repeating structure body 101.

It should be noted that in the case of the laser lamination molding method, a molded object such as the ridge filter 100 is desirably arranged and molded in a state inclined with respect to, at least, the X direction and the Z direction in an area where the molded object is arranged as described in FIG. 10. In other words, the ridge filter 100 is desirably molded in a state inclined with respect to the lamination direction (Z direction) of the resin 112. The inclined angle is desirably 1° to 45° with respect to the direction (the X direction or the Y direction) orthogonal to the lamination direction (Z direction) of the resin 112 (inclined with respect to the lamination direction (Z direction) by 45° to 89°). It is possible to reduce the warp at the time of molding and the warp at the time of cooling by inclining the ridge filter 100. In addition, the productivity of the ridge filter 100 can be improved by setting the inclined angle with respect to the direction (the X direction or the Y direction) orthogonal to the lamination direction (Z direction) to 1° to 45°. It should be noted that it has been confirmed that there is no effect on transmission characteristics of the proton beam 204 in the case where steps in accordance with the inclination become remarkable when being inclined and surface roughness is increased.

In addition, since a particle diameter of 30 to 150 μm (D50) is used in the case of powder molding, the thickness per layer is preferably set to 0.05 mm to 0.15 mm. When the thickness is smaller than 0.05 mm, the powder cannot be uniformly laid. When the thickness is larger than 0.15 mm, the intensity is decreased. In addition, as similar to the nozzle operation in the molten deposition method, it is preferable even in the case of the power lamination that the laser irradiation is alternately repeated in such a manner that the laser 134 is controlled on the first layer in the X direction and then is controlled on the next layer (second layer) in the Y direction. The voids 113 can be ununiformed, and the warp can be reduced by such an operation.

In addition, even in the case where the ridge filter 100 is produced (formed) by the laser lamination molding method, the warp is desirably corrected. In this case, the ratio of a sinter state is desirably increased by reducing the laser irradiation energy only for the bottom plate 102. The thickness of the bottom plate 102 is desirably 0.1 mm or larger and 1.2 mm or smaller, and it is preferable to satisfy the same relation as that shown in the molten deposition method from the viewpoint of the density, voids, and elastic modulus. It should be noted that even in the case of any one of the molten deposition method and the powder lamination method, it is preferable to mold the integrated frame 110 as shown in FIG. 4 at both ends in the X direction or the Y direction in order to secure the rigidity of the entire ridge filter 100. In addition, it is preferable to set the height of the integrated frame 110 higher than the height H of the repeating structure body 101 of FIG. 5 due to a possibility of destruction by being brought into contact with the repeating structure body 101. The frame 110 serves as a wall by setting the height of the integrated frame 110 higher than the height H of the repeating structure body 101. Thus, it is possible to reduce the possibility of destruction by being brought into contact with the repeating structure body 101.

Fourth Embodiment

Figure 11:
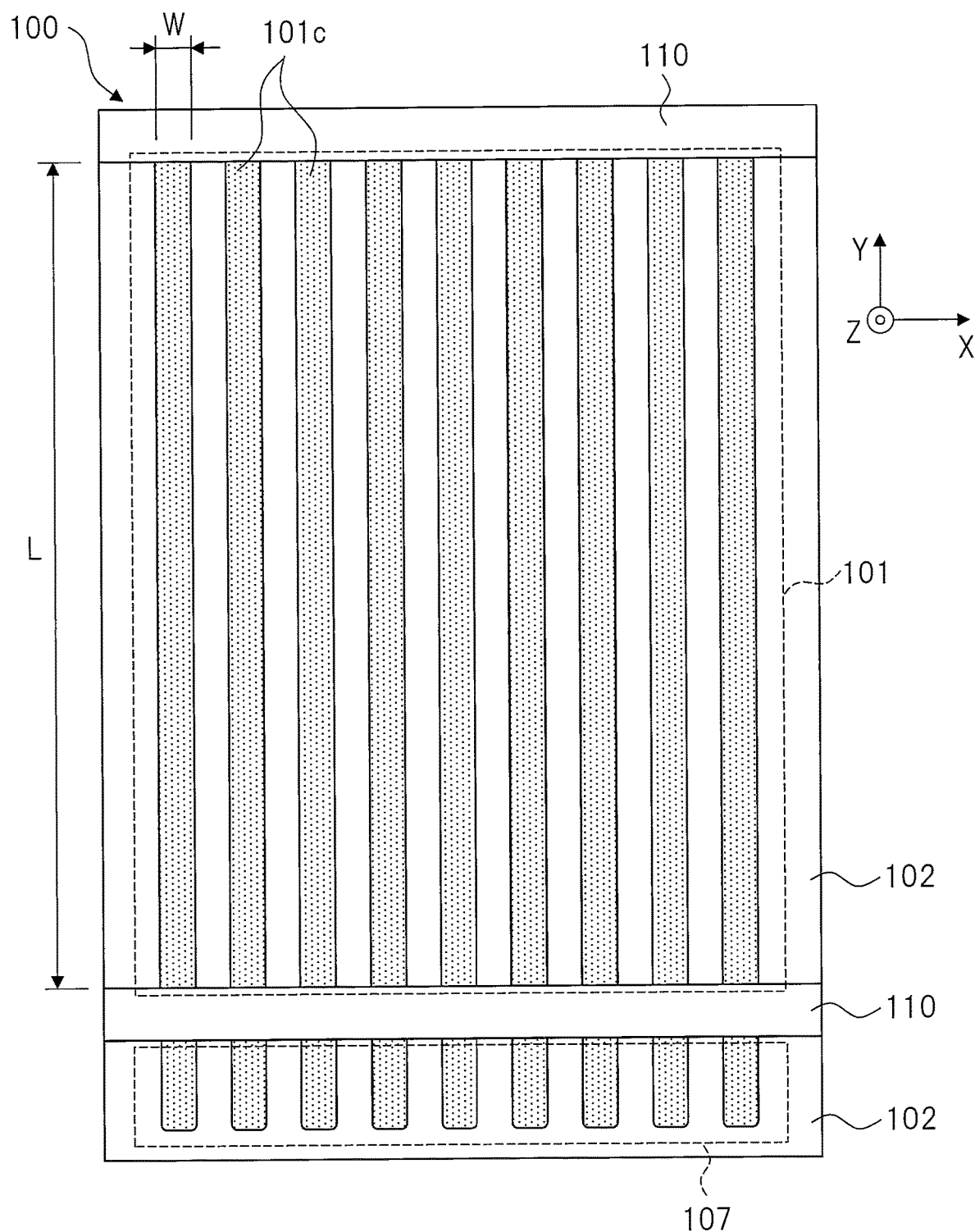
FIG. 11 is a plan view for showing an example of a structure of a ridge filter according to a fourth embodiment of the present invention.
Figure 12:
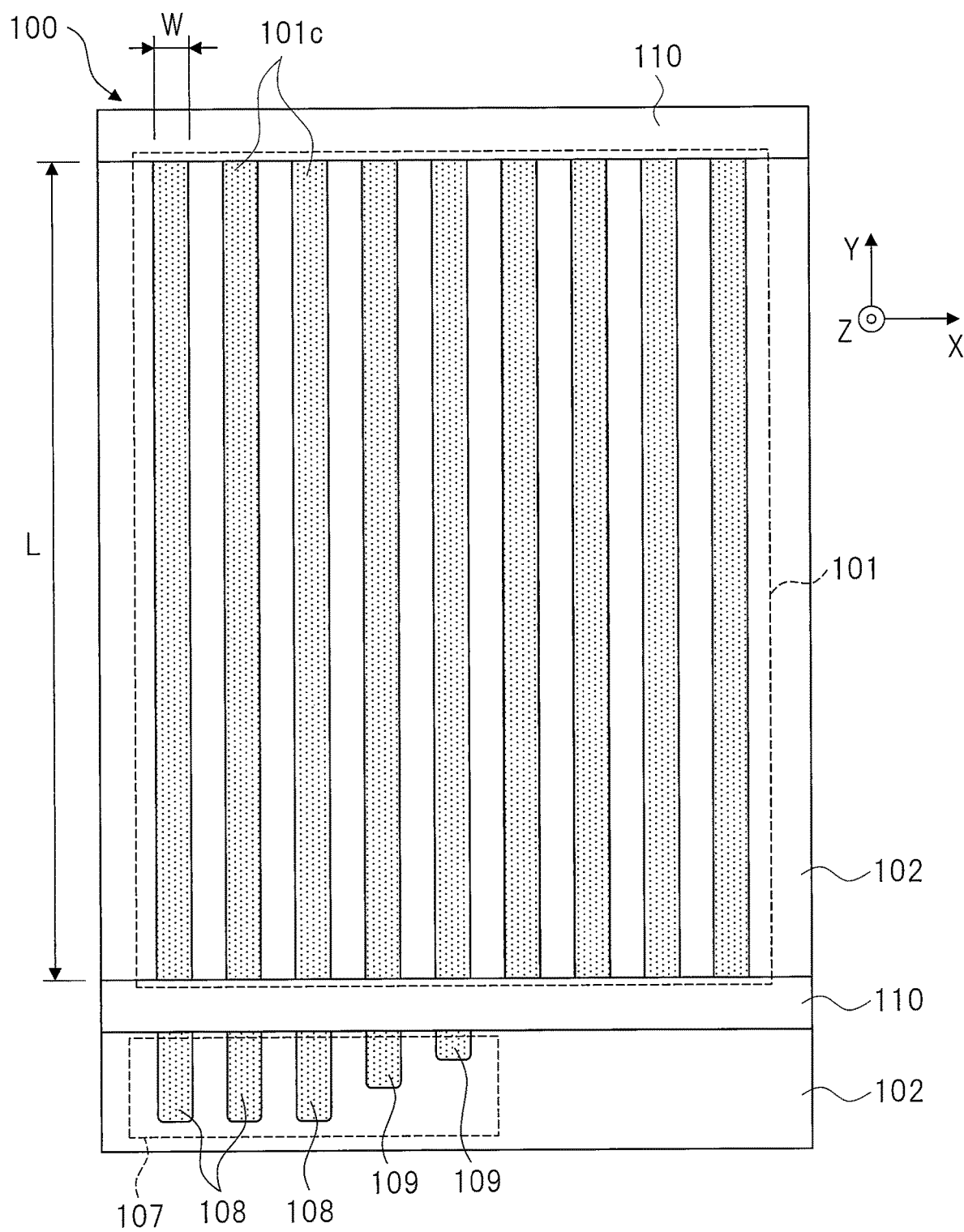
FIG. 12 is a plan view for showing a structure of a ridge filter according to a first modified example of the fourth embodiment of the present invention.
Figure 13:
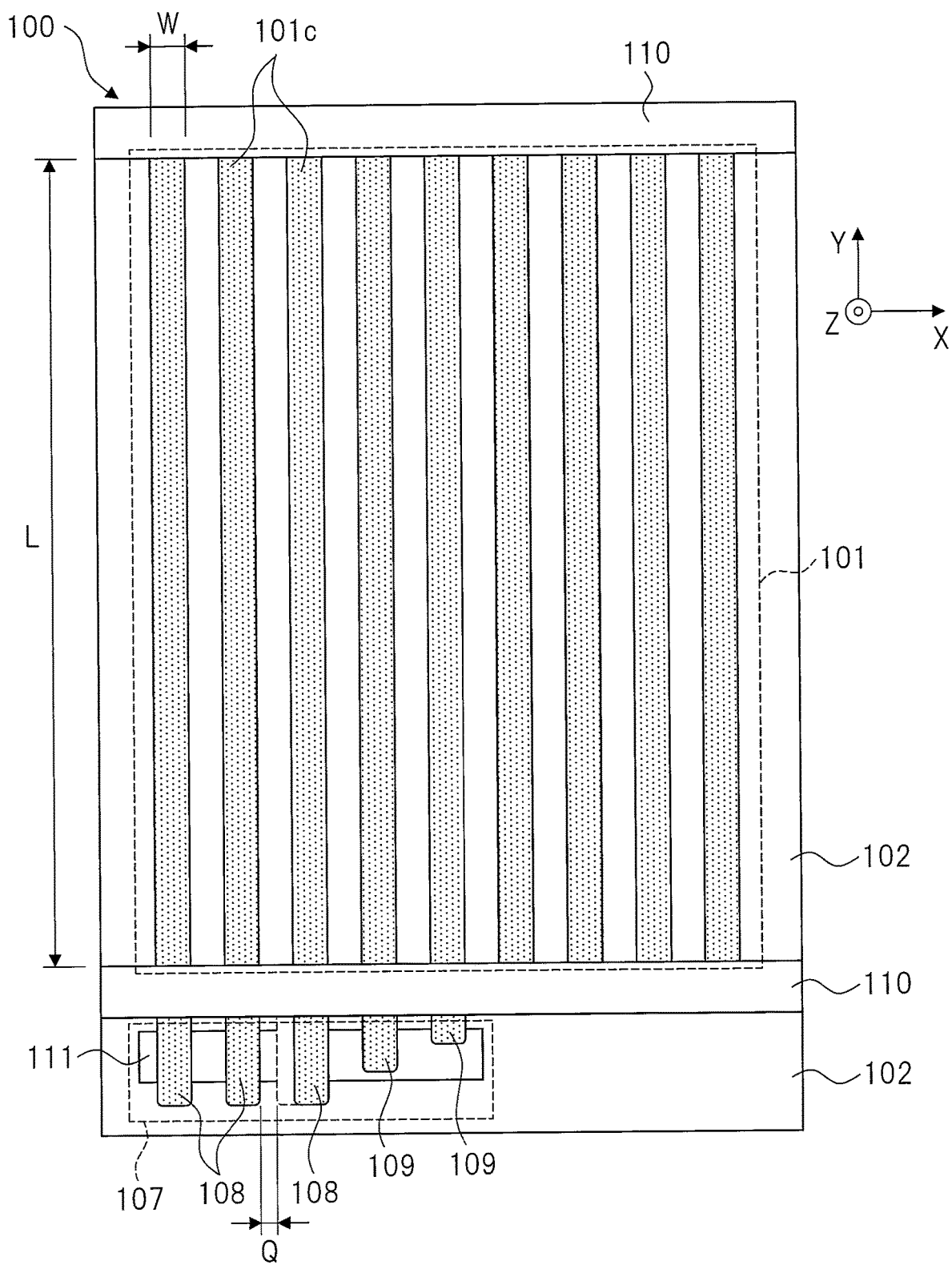
FIG. 13 is a plan view for showing a structure of a ridge filter according to a second modified example of the fourth embodiment of the present invention.

FIG. 11 is a plan view for showing an example of a structure of a ridge filter according to a fourth embodiment of the present invention, FIG. 12 is a plan view for showing a structure of a ridge filter according to a first modified example of the fourth embodiment of the present invention, and FIG. 13 is a plan view for showing a structure of a ridge filter according to a second modified example of the fourth embodiment of the present invention.

In the case where a ridge filter 100 is produced by a molten deposition method or a laser lamination molding method (powder lamination method), a relatively-free integrated shape can be obtained. However, for example, it is impossible to inspect the appearance of the structure shown above after molding. In consideration of such a case, as shown in FIG. 11, it is preferable to arrange a repeating structure body for inspection (third structure body) 107 on the outer side of a frame 110 of a repeating structure body 101 of the ridge filter 100. Namely, the repeating structure body for inspection 107 having the same shape as that of, at least, a part of the repeating structure body 101 is formed at a region where no proton beam 204 passes through on the outer side of the frame 110.

As described above, it is possible to optically inspect the pitch and shape of the repeating structure body for inspection 107 from an upper face or side face thereof by molding the repeating structure body for inspection 107 at a region where no proton beam 204 passes through on the outer side of the frame 110. Accordingly, it is possible to confirm whether or not the repeating structure body 101 is molded as designed.

In addition, only a part of operation does not become instable in lamination molding in the molding apparatus (for example, the lamination molding apparatus 120 or the lamination molding apparatus 130). On the other hand, there are many cases in which the molding apparatus stops halfway. Even in such a case, the shape of the repeating structure body for inspection 107 is measured (inspected) by setting the height of the repeating structure body for inspection 107 equal to or higher than that of the ridge filter 100. Accordingly, the structure and the accuracy of the repeating structure body 101 can be secured.

Namely, when the length of the proton beam 204 of the repeating structure body 101 in the incident direction is the thickness of the repeating structure body 101, the thickness of the repeating structure body for inspection 107 formed at a region where no proton beam 204 passes through is set equal to or larger than the thickness of the repeating structure body 101. Accordingly, it is possible to determine whether or not the structure of the repeating structure body 101 is final if the repeating structure body for inspection 107 is inspected from the outside. As a result, the structure and the accuracy of the repeating structure body 101 can be also secured as described above.

Further, it is preferable to arrange the repeating structure body for inspection 107 at the final position of a molding path. Namely, if the repeating structure body for inspection 107 is molded at the final position of the molding path and the shape of the repeating structure body for inspection 107 is confirmed from the outside, it is possible to confirm the acceptance decision for the shape of the repeating structure body 101 because the shapes of all the molded structure bodies are the same as that of the repeating structure body for inspection 107.

In addition, as shown in FIG. 12, a plurality of structure bodies for inspection (third structure bodies) 108 only the lengths of which are changed (lengthened) in the Y direction is prepared in the repeating structure body for inspection 107, and then a plurality of structure bodies for inspection (third structure bodies) 109 whose lengths in the Y direction are shorter than those of the structure bodies for inspection 108 may be arranged. In this case, by preparing, at least, three kinds of standards as the lengths in the Y direction, it is possible to observe from various directions, and to simply measure at a site using a caliper or the like.

In addition, the pitch interval of the extending part 101c in the repeating structure body 101 is important in characteristics in the ridge filter 100 of the fourth embodiment. However, a gap (a gap Q between the adjacent extending parts 101c shown in FIG. 13) in accordance with the pitch interval of the extending part 101c becomes important in some cases. In this case, as shown in FIG. 13, a through-hole 111 is provided at a part of the bottom plate 102 of the repeating structure body for inspection 107, so that it is possible to observe and recognize a gap amount (length of the gap Q) in accordance with the pitch interval of the extending part 101c of the repeating structure body for inspection 107 from the upper and lower sides using a microscope or the like. As a result, it is possible to inspect gap amounts in accordance with the pitch intervals of a plurality of extending parts 101c of the repeating structure body 101.

The invention made by the inventors has been concretely described above on the basis of the embodiments. However, the present invention is not limited to the above-described embodiments, and includes various modified examples. For example, the above-described embodiments have been described in detail to understandably describe the present invention, and are not necessarily limited to those including all the configurations described above.

In addition, a part of a configuration of an embodiment can be replaced by a configuration of the other embodiments, and a configuration of an embodiment can be added to a configuration of the other embodiments. In addition, other configurations can be added to, deleted from, or replaced by a part of a configuration of each embodiment. It should be noted that each member and relative sizes described in the drawings are simplified and idealized to understandably describe the present invention, and the shapes become more complicated when being mounted.

In the description of the first to fourth embodiments, the bottom plate 102 is provided on the lower face (second face) 101b side of the repeating structure body 101. However, the bottom plate 102 may be provided on the upper face (first face) 101a side.

The first to fourth embodiments describe a structure and a manufacturing method of a ridge filter 100 when producing the ridge filter 100 using a molten deposition method or a powder lamination method, and any shape of the structure of the repeating structure body for inspection 107 can be applied.

LIST OF REFERENCE SIGNS 100 ridge filter
101 repeating structure body (first structure body)
101a upper face (first face)
101b lower face (second face)
101c extending part
102 bottom plate (bottom part, second structure body)
107 repeating structure body for inspection (third structure body)
108 structure body for inspection (third structure body)
109 structure body for inspection (third structure body)
110 frame
111 through-hole
112 resin
113 void (gap)
120 lamination molding apparatus
121 nozzle
122 chamber
130 lamination molding apparatus
132 roller
134 laser
136 resin powder
204 proton beam
205 irradiation target

The invention claimed is:

1. A manufacturing method of a ridge filter formed by laminating resin, the method comprising the steps of:
    (a) discharging the molten resin from a nozzle;
    (b) after the step (a), forming a second structure body by sequentially repeating scanning of the nozzle and by lamination molding of the resin such that an extending direction of the resin in one layer of the second structure body is formed to alternately intersect with that in another layer in the second structure body in the lamination direction of the resin; and
    (c) after the step (b), forming a first structure body including a plurality of extending parts, each formed to extend in a single layer and parallel to the other extending parts, the first structure body formed of the laminating resin and extending along a direction intersecting the lamination direction of the resin.

2. The manufacturing method of a ridge filter according to claim 1, wherein
    the number of layers of laminated resins in the second structure body is an even number.

3. A ridge filter provided in a particle therapy system, the ridge filter comprising:
    a first structure body that includes a plurality of extending parts, each extending in a single layer and parallel to the other extending parts, the first structure body formed by laminating resin and extending along a direction intersecting a laminate direction of the resin; and
    a second structure body that is provided on one of a first face of the first structure body on the incident side of the proton beam and a second face opposite to the first face, wherein
    the first structure body and the second structure body are formed of laminates integrally formed by laminating molten resin, and the second structure body is directly attached to the plurality of extending parts,
    wherein the second structure body is formed of a laminate of resin, and an extending direction of the resin in one layer of the second structure body is formed to alternately intersect with that in another layer in the second structure body in the lamination direction of the resin.

4. The ridge filter according to claim 3, wherein
    the number of layers of laminated resins in the second structure body is an even number.

5. The ridge filter according to claim 3, wherein
    the elastic modulus of the second structure body is smaller than that of the first structure body.

6. The ridge filter according to claim 3, wherein
    the thickness of the second structure body is 0.1 mm or larger and 1.2 mm or smaller.

7. The ridge filter according to claim 6, wherein
    a frame is arranged around the first structure body.

8. The ridge filter according to claim 7, wherein
a third structure body having the same shape as that of, at least, a part of the first structure body is formed at a region on the outer side of the frame where no proton beam passes through.

9. The ridge filter according to claim 8, wherein
when the length of the first structure body in the incident direction of the proton beam is assumed as a thickness, the thickness of the third structure body formed at the region where no proton beam passes through is equal to or larger than that of the first structure body.

* * * * *